United States Patent [19]

Karcher et al.

[11] Patent Number: 5,319,148
[45] Date of Patent: Jun. 7, 1994

[54] PREPARATION OF PYROCATECHOL MONOETHERS AND PYROCATECHOLS

[75] Inventors: Michael Karcher, Dossenheim; Horst Zimmermann, Mannheim; Jochem Henkelmann, Ludwigshafen, all of Fed. Rep. of Germany

[73] Assignee: BASF Aktiengesellschaft, Ludwigshafen, Fed. Rep. of Germany

[21] Appl. No.: 25,732

[22] Filed: Mar. 2, 1993

Related U.S. Application Data

[63] Continuation of Ser. No. 833,171, Feb. 10, 1992, abandoned.

[30] Foreign Application Priority Data

Feb. 10, 1992 [DE] Fed. Rep. of Germany ....... 4104417

[51] Int. Cl.$^5$ .................... C07C 41/09; C07C 41/28
[52] U.S. Cl. .................... 568/653; 568/652; 568/766; 568/772; 568/650; 568/763
[58] Field of Search .......................... 568/766

[56] References Cited

U.S. PATENT DOCUMENTS

| Re. 29,200 | 5/1977 | McKague et al. ................ 568/652 |
| 3,689,570 | 9/1972 | Gradeff et al. ................. 260/613 D |
| 3,801,651 | 4/1974 | Adolphen et al. ............... 260/613 |
| 3,895,076 | 7/1975 | Bauer et al. .................... 260/613 D |
| 4,204,076 | 5/1980 | Konz et al. ..................... 568/651 |
| 4,254,288 | 3/1981 | Gladwin ......................... 568/653 |

FOREIGN PATENT DOCUMENTS

| 2140738 | 8/1971 | Fed. Rep. of Germany . |
| 2703077 | 1/1977 | Fed. Rep. of Germany . |
| 51-215 | 8/1976 | Japan ............................ 568/772 |
| 2051068 | 1/1981 | United Kingdom . |

OTHER PUBLICATIONS

McOnie, *Proctective Groups in Organic Chemistry*, pp. 327-328, (1973).
"Hydroquinone and Pyrocatechol Production by Direct Oxidation of Phenol"; Varagnat, Ind. Eng. Chem., Prod. Res. Dev., vol. 15, No. 3, 1976.
*Chem. Abst.*, vol. 82, No. 23, Jun. 9, 1975, p. 558.

*Primary Examiner*—Marianne M. Cintins
*Assistant Examiner*—Margaret J. Page
*Attorney, Agent, or Firm*—Keil & Weinkauf

[57] ABSTRACT

The preparation of pyrocatechol monoethers or pyrocatechols of the formula Ia or Ib respectively

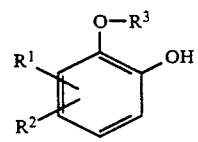

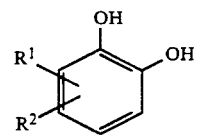

( $R^1$ and $R^2$=H or $C_1$—$C_8$-hydrocarbon radicals; $R^3$=$C_1$—$C_8$-hydrocarbon radical ) by rearranging a 2-hydroxycyclohexanone dialkyl ketal II

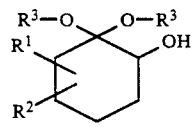

a) in the gas phase in the presence of a platinmetal or in the presence of a compound of one of these metals as catalyst in order to obtain a compound Ia, or
b) carrying out step a) in the presence of water in order to obtain a compound Ib. The products are used as intermediates in the synthesis of pharmaceuticals, fragrances and flavors.

4 Claims, No Drawings

PREPARATION OF PYROCATECHOL MONOETHERS AND PYROCATECHOLS

This application is a continuation of application Ser. No. 07/833,171, filed on Feb. 10, 1992, now abandoned.

The present invention relates to a novel process for the preparation of pyrocatechol monoethers or pyrocatechols of the formula Ia or Ib respectively

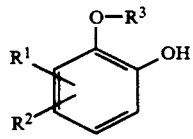

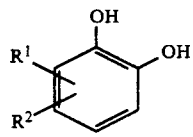

where $R^1$ and $R^2$ are hydrogen or $C_1$—$C_8$-hydrocarbon radicals, and $R^3$ is a $C_1$—$C_8$-hydrocarbon radical.

The compounds Ia and Ib are known and are used as intermediates in the synthesis of pharmaceuticals, fragrances and flavors.

Ind. Eng. Chem., Prod. Res. Dev., 15 (3) (1976), 212, describes the catalytic hydroxylation of phenol using hydrogen peroxide in the presence of phosphoric acid and perchloric acid to give pyrocatechol and hydroquinone.

However, this synthesis has the disadvantage of giving approximately equal amounts of hydroquinone in addition to the pyrocatechol.

DE-A-20 07 737 discloses the partial etherification of pyrocatechol using an alkyl halide in weakly aqueous-alkaline medium to give pyrocatechol monoalkyl ethers.

A further possible synthesis of pyrocatechol monomethyl ethers is the partial methylation of pyrocatechol using methanol at elevated temperature in the presence of a catalyst such as phosphoric acid (DE-A-12 25 665) or a phosphate, such as boron phosphate (DE-A-21 40 738).

However, the processes disclosed hitherto for the preparation of pyrocatechol monoalkyl ethers are unsatisfactory due to the formation of dialkyl ethers which occurs to an increased extent at high conversions, and the associated separation problems, and due to the high consumption of alkylating agent.

Furthermore, DE-A-27 03 077 discloses the conversion of cyclohexane-1,4-dione tetramethyl diketal into hydroquinone dimethyl ether by catalytic dehydrogenation and elimination of methanol in the liquid phase.

It is therefore an object of the present invention to provide a simpler and more economical process for the preparation of pyrocatechol monoethers Ia and pyrocatechols Ib.

We have found that this object is achieved by a novel process for the preparation of pyrocatechol monoethers or pyrocatechols of the formula Ia or Ib respectively

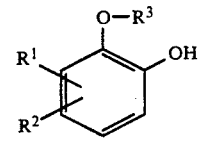

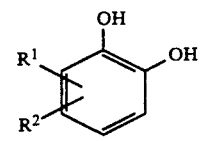

where $R^1$ and $R^2$ are hydrogen or $C_1$—$C_8$-hydrocarbon radicals, and $R^3$ is a $C_1$—$C_8$-hydrocarbon radical, which comprises rearranging a 2-hydroxycyclohexanone dialkyl ketal of the formula II

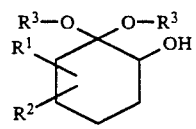

a) in the gas phase in the presence of a platinum metal or in the presence of a compound of one of these metals as catalyst in order to obtain a compound Ia, or b) carrying out step a) in the presence of water in order to obtain a compound Ib.

The process according to the invention can be illustrated as follows:

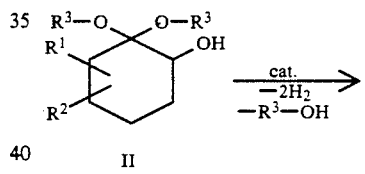

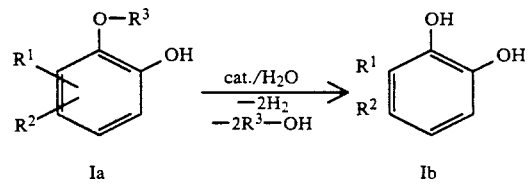

The starting compounds II are known or can be obtained by known methods, for example by electrochemical oxidation of cyclohexanone using an alkanol in the presence of an auxiliary electrolyte and water (earlier German patent application P 4017576.6).

For economic reasons, preferred compounds II of those defined are those in which the radicals have the following meanings:

hydrogen;

$C_1$-$C_8$-alkyl, preferably $C_1$-$C_4$-alkyl, particularly preferably $C_1$-$C_2$-alkyl, such as ethyl and in particular methyl;

$C_2$-$C_8$-alkenyl, preferably $C_2$-$C_6$-alkenyl, particularly preferably $C_2$-$C_4$-alkenyl, such as propenyl, butenyl and in particular ethenyl;

$C_2$-$C_8$-alkynyl, preferably $C_2$-$C_6$-alkynyl, particularly preferably $C_2$-$C_4$-alkynyl, such as propynyl, butynyl and in particular ethynyl;

$C_3$–$C_8$-cycloalkyl, preferably $C_5$–$C_7$-cycloalkyl, such as cyclopentyl, cycloheptyl in and particular cyclohexyl;

$C_7$–$C_8$-arylalkyl, preferably phenylethyl and particular benzyl;

aryl, preferably phenyl.

In view of the desired products I, 2-hydroxycyclohexanone dimethyl ketal is particularly preferred.

For technical reasons associated with the process, it is advisable to employ the 2-hydroxy-cyclohexanone dimethyl ketal II in the form of a solution and to evaporate it together with the solvent. Preferred solvents for obtaining the compounds Ia are dioxane and tetrahydrofuran. Particularly good results are achieved using methanol.

In order to obtain the compounds Ib, water, alone or in mixtures, is the preferred solvent.

In general, the solutions contain from 10 to 80% by weight, preferably from 20 to 50% by weight, of compound II.

The catalyst to be employed in the process according to the invention is a platinum metal or a compound thereof.

The catalyst can be employed in the form of a metal, salt, oxide or complex.

Suitable catalysts in metallic form are preferably platinum and in particular palladium.

The metal is preferably used in the form of a supported catalyst on a carrier having a very large surface area, preferably alumina, silica, titanium oxide, zinc oxide, lanthanum oxide, zirconium oxide, barium sulfate, aluminum silicate, spinels or mixtures of these materials, and in particular charcoal, where palladiun on charcoal should be particularly emphasized.

The supported catalyst preferably contains from 0.2 to 5% by weight, in particular from 0.6 to 1.5% by weight, of active metal, based on the sum of carrier and catalytically active metal, calculated as the metal.

The catalyst may be employed either as 2 mm to 4 mm pellets, tablets having a diameter of from 3 to 5 mm granules having a particle size of from 0.05 to 1 , preferably from 0.1 to 0.5 , as the maximum diameter or as a powder having a particle size of from 0.05 to 0.5 nn, the powder also being suitable as a fluidized bed catalyst.

If the catalyst metal as defined is used in the form of a compound, complexes of ruthenium or rhodium, for example rhodium acetylacetonate, and complexes containing at least two ligands of the triorganyl-phosphorus and carbon monoxide type as further ligands are particularly suitable.

The space velocity in the continuous process is from 0.1 to 20 kg, preferably from 1 to 5 kg, of compound II per kg of the metal.

It is very advantageous economically to employ the platinum metal catalyst in partially deactivated form since this results in higher product selectivity, in particular in the case of highly-active metals.

Suitable deactivating catalyst poisons are preferably sulfur, selenium, tellurium, iodine and barium sulfate, which are generally employed in amounts of from 0.05 to 0.3% by weight, preferably from 0.1 to 0.15% by weight, of compound II.

The reaction is usually carried out at from 200 to 400° C., preferably at from 240° to 340° C., in particular at from 280° to 300C. Since the reaction is carried out in the gas phase, the temperature must at least be sufficient to ensure full evaporation of the starting compound II.

The reaction is expediently carried out at atmospheric pressure, but reduced pressure or slightly superatmospheric pressure can also be used, for example a pressure in the range from 10 mbar to 20 bar.

The reaction time is normally from 0.1 to 60 seconds, usually from 1 to 5 seconds.

In order to suppress dehydration processes, it may be expedient to carry out the reaction in the presence of basic additives. Suitable compounds for this purpose are nitrogen bases, such as triethylnine, cyclohexylamine and pyridine. Preference is given to alkali metal hydroxides, such as sodium hydroxide solution or potassium hydroxide solution, and alkali metal alkoxides, such as sodium methoxide, potassium methoxide and sodium ethoxide. Particularly preferred bases are alkali metal carbonates, such as sodium carbonate and in particular potassium carbonate.

These are usually employed in amounts of from 0.1 to 3.0% by weight, preferably from 1.0 to 1.5% by weight, based on the compound II.

The reaction is carried out in the gas phase; a fixed-bed reaction or a gas-phase reaction in a fluidized bed are possible.

In order to maintain the catalyst activity during the dehydrogenation, it is advisable to use a carrier gas comprising hydrogen or a mixture of hydrogen and nitrogen or argon.

An economically very advantageous embodiment of the process according to the invention is a fixed-bed reaction in which the 2-hydroxycyclohexanone dialkyl ketal II, if desired in solution, is evaporated and passed, as a gas phase, if necessary with the aid of a carrier gas, over a solid catalyst.

If compound II is added without using a solvent, water in the form of steam is introduced in order to isolate the products Ib.

The mixture can be worked up to give the products in a conventional manner, generally by fractional distillation, if necessary with subsequent extraction.

The pyrocatechol monoethers Ia and pyrocatechols Ib obtainable in a simple and economical manner by the process according to the invention can be used as intermediates in the synthesis of pharmaceuticals, such as Verapamil, fragrances and flavors, such as vanillin.

EXAMPLES

1. Preparation of pyrocatechol monomethyl ether

A solution of 6 g of 2-hydroxycyclohexanone dimethyl ketal in 24 g of methanol was evaporated at 300° C. over the course of one hour and passed, together with 60 l of a 1:1 mixture of hydrogen and nitrogen as carrier gas, within 2 seconds over 100 g of a solid palladium catalyst (1% by weight of palladium on charcoal; poisoned with 0.1% by weight of sulfur; basic additive: 1.5% by weight of potassium carbonate).

Conventional work-up by fractional distillation gave pyrocatechol monomethyl ether in a yield of 63.6%.

2. Preparation of pyrocatechol

A procedure similar to that of Example 1, but in aqueous solution, gave a pyrocatechol yield of 74.1%.

Use of a 9:1 mixture of methanol and water gave a mixture comprising 30.70% of pyrocatechol monomethyl ether and 23.3% of pyrocatechol.

We claim:

1. A gas phase process for the preparation of pyrocatechol monoethers or pyrocatechols of the formula Ia or Ib respectively

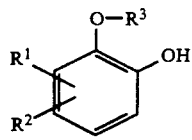
Ia

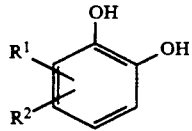
Ib where $R^1$ and $R^2$ are hydrogen or $C_1$-$C_8$-hydrocarbon radicals, and $R^3$ is a $C_1$-$C_8$-hydrocarbon radical, which comprises dissolving a 2-hydroxycyclohexanone dialkyl ketal of the formula II

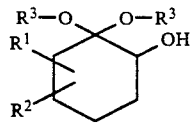
II $R^1$, $R^2$ and $R^3$ having the meanings given above in a solvent; heating the solution sufficiently to evaporate the solution, and passing the vapors over a platinum metal catalyst or a platinum metal compound catalyst for 0.1 to 60 seconds to obtain the final product.

2. A process as set forth in claim 1, wherein $R^1$ and $R^2$ are hydrogen and $R^3$ is methyl.

3. A process as set forth in claim 1, wherein the solvent is methanol, dioxane or tetrahydrofuran, and wherein a pyrocatechol monoether of the formula Ia is produced.

4. A process as set forth in claim 1, wherein the process is carried out in the presence of water and a pyrocatechol of the formula Ib is produced.

* * * * *

UNITED STATES PATENT AND TRADEMARK OFFICE
CERTIFICATE OF CORRECTION

PATENT NO.: 5,319,148

DATED: June 7, 1994

INVENTOR(S): KARCHER et al.

It is certified that error appears in the above-identified patent and that said Letters Patent is hereby corrected as shown below:

<u>TITLE PAGE</u>

In the Abstract, 7 lines from the bottom, "platinmetal" should be --platinum metal--.

Signed and Sealed this

Fourth Day of October, 1994

Attest:

BRUCE LEHMAN

Attesting Officer

Commissioner of Patents and Trademarks